(12) United States Patent
Drumm et al.

(10) Patent No.: US 8,041,089 B2
(45) Date of Patent: Oct. 18, 2011

(54) METHOD AND DEVICE FOR REGISTERING AN ANATOMICAL STRUCTURE USING MARKERS

(75) Inventors: Peter Drumm, München (DE); Markus Hepke, München (DE)

(73) Assignee: Brainlab AG, Feldkirchen (DE)

( * ) Notice: Subject to any disclaimer, the term of this patent is extended or adjusted under 35 U.S.C. 154(b) by 999 days.

(21) Appl. No.: 11/943,813

(22) Filed: Nov. 21, 2007

(65) Prior Publication Data

US 2008/0137931 A1    Jun. 12, 2008

Related U.S. Application Data

(60) Provisional application No. 60/867,613, filed on Nov. 29, 2006.

(30) Foreign Application Priority Data

Nov. 24, 2006   (EP) .................................... 06024421

(51) Int. Cl.
*G06K 9/00* (2006.01)
(52) U.S. Cl. ........ 382/128; 382/131; 382/132; 382/154; 382/294
(58) Field of Classification Search ................. 382/128, 382/154, 285
See application file for complete search history.

(56) References Cited

U.S. PATENT DOCUMENTS

| | | | |
|---|---|---|---|
| 5,636,255 A | 6/1997 | Ellis | |
| 5,799,055 A | 8/1998 | Peshkin et al. | |
| 5,951,475 A * | 9/1999 | Gueziec et al. | ............... 600/425 |
| 6,044,132 A | 3/2000 | Navab | |
| 6,243,439 B1 | 6/2001 | Arai et al. | |
| 6,359,960 B1 | 3/2002 | Wahl et al. | |
| 2001/0021806 A1 | 9/2001 | Gueziec et al. | |
| 2003/0029464 A1 | 2/2003 | Chen et al. | |

FOREIGN PATENT DOCUMENTS

| | | |
|---|---|---|
| DE | 199 10 107 | 9/1999 |
| DE | 199 36 364 | 2/2001 |
| WO | 95/15729 | 6/1995 |
| WO | 95/20343 | 8/1995 |
| WO | 01/34051 | 5/2001 |

* cited by examiner

*Primary Examiner* — Tom Y Lu
(74) *Attorney, Agent, or Firm* — Renner, Otto, Boisselle & Sklar, LLP

(57) ABSTRACT

A method for registering an anatomical structure using at least one marker attached to the structure includes: obtaining a three-dimensional model of the structure via an imaging method; obtaining at least two two-dimensional recordings of the structure from different angles; and ascertaining a spatial position and location of the three-dimensional model or a position and location of the three-dimensional model in a patient coordinate system based on a matching method that uses the position of the at least one marker in the at least two two-dimensional mappings such that the three-dimensional model of the structure matches the structure.

16 Claims, 5 Drawing Sheets

METHOD AND DEVICE FOR REGISTERING AN ANATOMICAL STRUCTURE USING MARKERS

RELATED APPLICATION DATA

This application claims priority of U.S. Provisional Application No. 60/867,613 filed on Nov. 29, 2006, which is incorporated herein by reference in its entirety.

FIELD OF THE INVENTION

The present invention relates to medical registration of anatomical structures using markers.

BACKGROUND OF THE INVENTION

Prior to surgery, it is often necessary to register an anatomical structure within a medical workspace, i.e., to determine a spatial location of the structure or of a partial region of the structure, such as a three-dimensional position of characteristic points or landmarks on the structure. These characteristic points or landmarks can be used in a hip operation, for example, to determine the spatial location of characteristic planes. From the location of the characteristic planes, the inserted position of a hip joint cavity can be determined.

If, in a hip operation, recordings are taken of the pelvis using a C-arm, then it is difficult or impossible to identify a characteristic or unique contour of the pelvis due to the different types of tissues and operating instruments that may be present. It also can be difficult to detect a contour or characteristic point since the anatomical structures are different for different patients, such that when registering the anatomical structure inaccuracies may be introduced. This can cause problems during or after surgery.

A method and device for registering a pelvis are known from WO 2005/084541, wherein a pointer comprising trackable markers that are detectable by a tracking system is used for acquiring points.

SUMMARY OF THE INVENTION

In a method for registering a structure, such as an anatomical structure, for example, it is possible to detect a contour in the structure itself or in a three-dimensional model of the structure and/or one or more landmarks. These contours and/or landmarks can be detected using at least two two-dimensional recordings obtained from an imaging method, and the structure can be registered by fixing one or more markers, such as radio-opaque markers, for example, on or in the structure (e.g., inserting the markers into the structure). The markers can be detected or identified by the imaging method used to obtain the two-dimensional recordings.

The marker or markers, for example, can be inserted into a bone or into the surface of the bone of a structure (e.g., a pelvis), preferably at a characteristic point or characteristic line, such that it is no longer necessary to detect the characteristic point or landmark when the corresponding marker or a group of markers is recorded. The positions of the markers in the at least two two-dimensional recordings of the structure can be rear-projected, and the intersection points resulting from the rear-projection can be compared with a three-dimensionally detected structure obtained using a CT method. The respective marker positions then can be matched so as to register the structure.

It is, however, not absolutely necessary to record a model and/or pre-operative image data sets. Even during the operation, the marker positions alone can define characteristic planes and, for example, planes that define the location or orientation of the object such as for example the mid-sagittal plane or the frontal pelvis plane, straight lines or points such as for example spinal points, in registered 2D images, which can be sufficient for the operation. Additionally, an image data set such as a CT data set, for example, also can be registered using the previously inserted marker positions.

In particular, when, prior to performing the method in accordance with the invention, the structure to be registered has been recorded with attached or inserted markers, then, in order to generate a three-dimensional computer model of the structure with the inserted markers, a known matching method can quickly and easily ascertain how the markers, which are visible on the at least two two-dimensional recordings of the structure, are assigned to the three-dimensional computer model. From this, it is then possible to ascertain the position of one or more characteristic points or landmarks that have a locational relationship with respect to the markers that are known from the three-dimensional recording of the structure. It is thus possible to determine known geometries, lines or points of a structure by means of two fluoroscopic images, for example, without using a pointer or the like to identify the characteristic points or landmarks on the structure.

If, for example, a pelvis is to be registered, then the pelvic contour can be detected in 2D images of the patient (which may be obtained intra-operatively) from which characteristic planes, for example, can be calculated as additional information. The 2D images can be registered via a reference on the patient, such as for example a reference star fixed on the patient, and wherein the fluoroscopic kit on the C-arm is already or can be automatically registered. Additional information, such as for example body planes obtained from the pelvic contour in the registered images, also can be used for orientating the implant components.

If a calibrated recording method or a calibrated recording device (e.g., a calibrated C-arm to which a number of markers are attached that can be identified by a navigation system) is used to generate the at least two two-dimensional recordings of the structure, then it is possible to determine or calculate the three-dimensional positions of the markers from the two-dimensional marker positions in the recordings or images, for example by rear-projection. This can be accomplished, for example, based on the registered recordings or fluoroscopic images taken from at least two different viewing directions, and in which markers connected to the structure are visible. The three-dimensional positions of the markers can thus be spatially ascertained. Further, and after a matching method using a previously obtained three-dimensional recording of the structure, the position and orientation of the three-dimensional structure can be spatially determined from the marker positions ascertained in this way, thus enabling the structure to be automatically registered. Using the method described herein, it is thus possible to easily register a structure, since only the position of one or more markers are ascertained. It is not necessary to detect a contour, which for example changes in accordance with the direction of the respective two-dimensional recording, and match it to a three-dimensional computer model.

The at least two two-dimensional recordings of the structure can be obtained from different directions using a calibrated x-ray source and a corresponding calibrated detector, such as for example a calibrated C-arm, wherein two transformation matrices of the respective x-ray recordings are known. The coordinates of the images and also the information in the images can be transformed by these two matrices into a patient coordinate system. In the patient coordinate system, the transformed information can be matched with a three-dimensional computer model obtained from a previously obtained CT or MR recording, for example.

The method described herein, for example, also can be performed using only one marker, if one or more landmarks are acquired by other methods, for example, via a pointer.

Objects made of tantalum, such as for example tantalum spheres, preferably having a diameter of less than 1 mm, are preferably used as markers and inserted into the bone or surface of the bone. Using tantalum markers that are inserted into a bone and localized by means of a pointer is known from WO 97/32522. Equally, cuboids or other edged objects which ensure a good anchoring in the bone, for example, also can be used as markers. A marker that is fixed in the bone by rotation or some other movement is also conceivable.

Also provided herein is a computer program which, when it is loaded onto a computer or is running on a computer, performs the method as described herein, and a program storage medium or computer program product comprising such a program.

A device for registering an anatomical structure comprises a recording unit for generating at least two two-dimensional mappings of the structure using recordings from different directions, such as for example a C-arm. The C-arm can be connected to a computational unit that has a three-dimensional model of the structure to be registered stored in memory (e.g., in a database). This three-dimensional model of the structure, for example, may have been generated by a CT scanner connected to the computational unit. The device also can comprise a navigation system for detecting the position of markers that, for example, reflect or emit visible or infrared light. One or more markers can be attached to the recording device, such as for example to the C-arm, such that calibrated recordings (e.g., calibrated fluoroscopic shots) can be generated and transmitted to the computational unit. The computational unit then can register the structure from the calibrated recordings of the structure and the three-dimensional model of the structure using the method described herein. The computational unit also can assign the position and orientation of the three-dimensional model to the actually present structure recorded from different directions by the recording device, such that ideally, the model and the actually present structure completely match.

BRIEF DESCRIPTION OF THE DRAWINGS

The forgoing and other features of the invention are hereinafter discussed with reference to the drawings.

DETAILED DESCRIPTION

Figure 1:
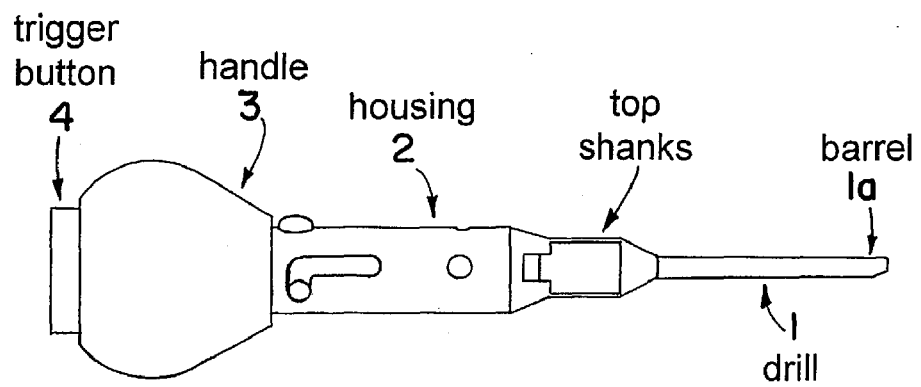
FIG. 1 is a diagram of an exemplary injection instrument for inserting markers.

FIG. 1 illustrates an exemplary injection device for inserting spherical tantalum markers into a bone. The injection device includes a hollow drill 1 having an opening 1a at its tip. One or more tantalum spherule 5 (FIG. 2) can be dispensed through the opening 1a once the drill 1 has drilled a recess or hole into a bone 6 (e.g., to a depth of about 3 mm). The drill 1 can be detachably fixed on a housing 2, which includes a handle 3 and a trigger button 4. The drill 1 can be rotated either by manually operating the handle 3 or by a motor provided in the housing 2 of the instrument. At the desired depth of penetration, the button 4 can be operated, which inserts the tantalum sphere 5 into the bone 6.

Figure 2:
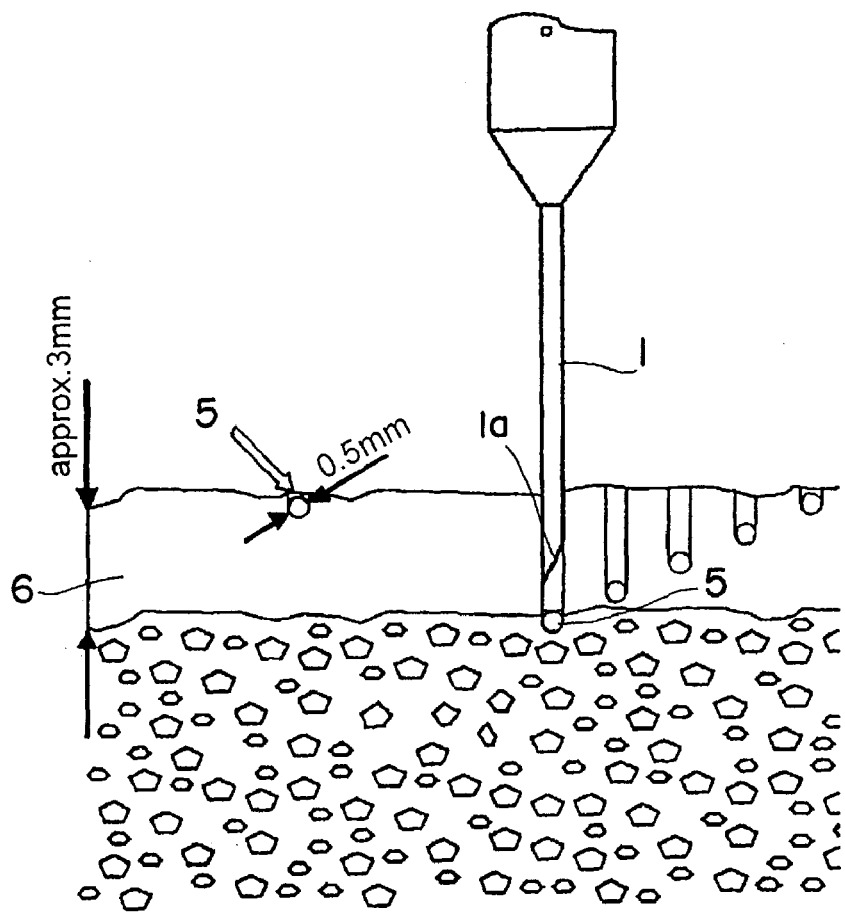
FIG. 2 is a cross-sectional view of an exemplary bone, together with the injection instrument of FIG. 1.

FIG. 2 illustrates a cross-sectional view of the drill 1 penetrating an approximately 3 mm thick compact bone layer in order to insert the spherical tantalum marker 5 (which has a diameter of about 0.5 mm) into the bone 6. A marker 5 inserted in this way sits securely in the bore formed in the bone 6 via a press or interference fit.

Figure 3:
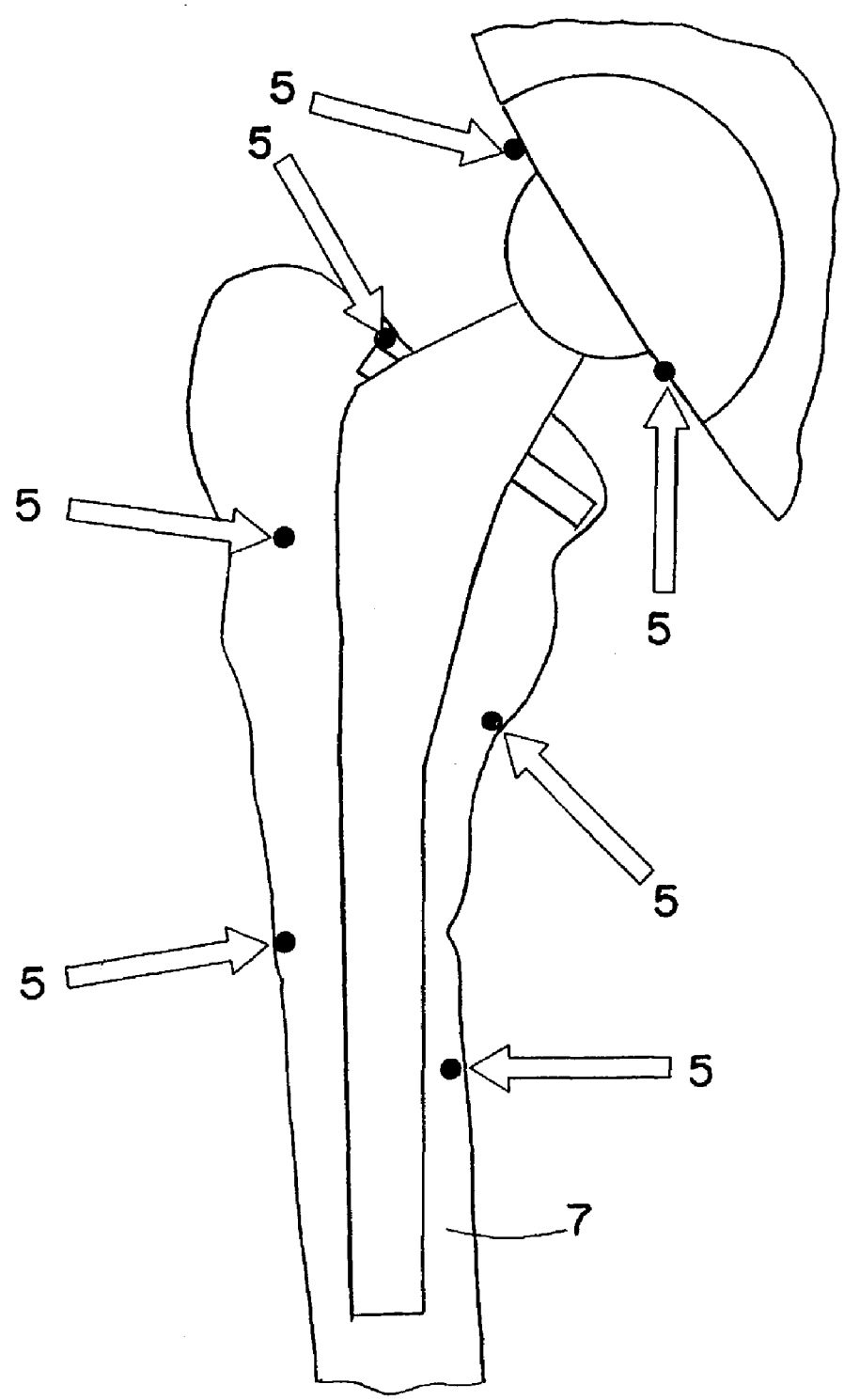
FIG. 3 is an x-ray recording of an exemplary femur comprising inserted tantalum markers.

If, as shown in FIG. 2, a number of tantalum markers 5 are inserted into the bone 6, then these markers 5 can easily be identified in a two-dimensional x-ray image of the bone structure. Such a two-dimensional x-ray image is shown in the x-ray recording of the femur 7 in FIG. 3. The coordinates of the centers of mass of the spherical markers 5 can be calculated and, when a number of calibrated x-ray recordings have been generated, the coordinates can be transformed into a patient coordinate system. If a number of markers 5 are present or if other characteristic points or landmarks on the structure are additionally acquired using known methods, such as for example acquiring points using a pointer, the anatomical structure can be registered as described herein.

Figure 4B:
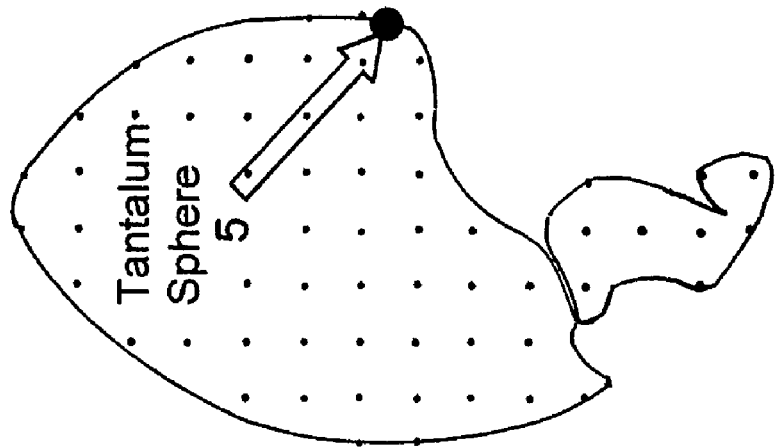
FIGS. 4A and 4B illustrate the mapping of a tantalum sphere in the spina iliaca.
Figure 4A:
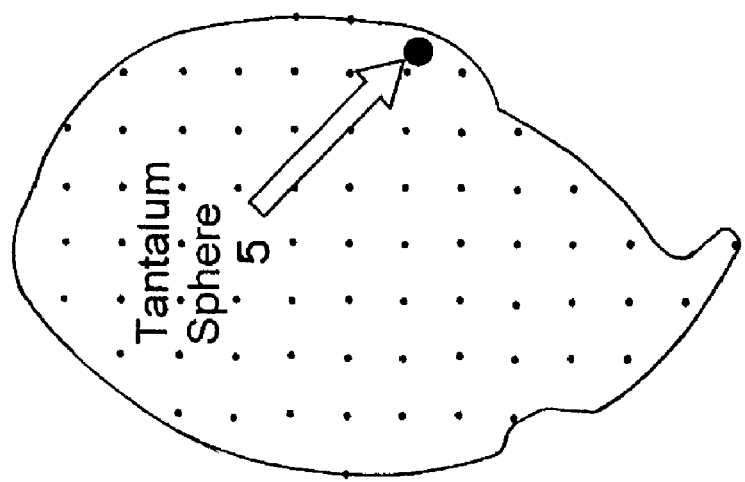

FIGS. 4A and 4B show an enlarged representation of the mapping of a tantalum marker 5 in the spina iliaca from two different directions, wherein the position of the tantalum marker 5 in three-dimensional space can be determined from the two calibrated recordings shown in FIGS. 4A and 4B. This can be accomplished, for example, by rear-projecting the marker position ascertained in the two two-dimensional recordings. In hip surgery wherein the patient is positioned laterally, it is not possible to reach both sides of the patient with, for example, a mechanical pointer. However, it is possible to ascertain the position of the spina iliaca in the patient coordinate system, including both the accessible portion and the inaccessible healthy side (on which the patient is lying) from the two recordings shown in FIGS. 4A and 4B. Therefore, it is possible to register the pelvis from the landmark ascertained in this way together with another landmark which, for example, is likewise marked by tantalum markers 5 or acquired by means of a pointer.

Figure 5:
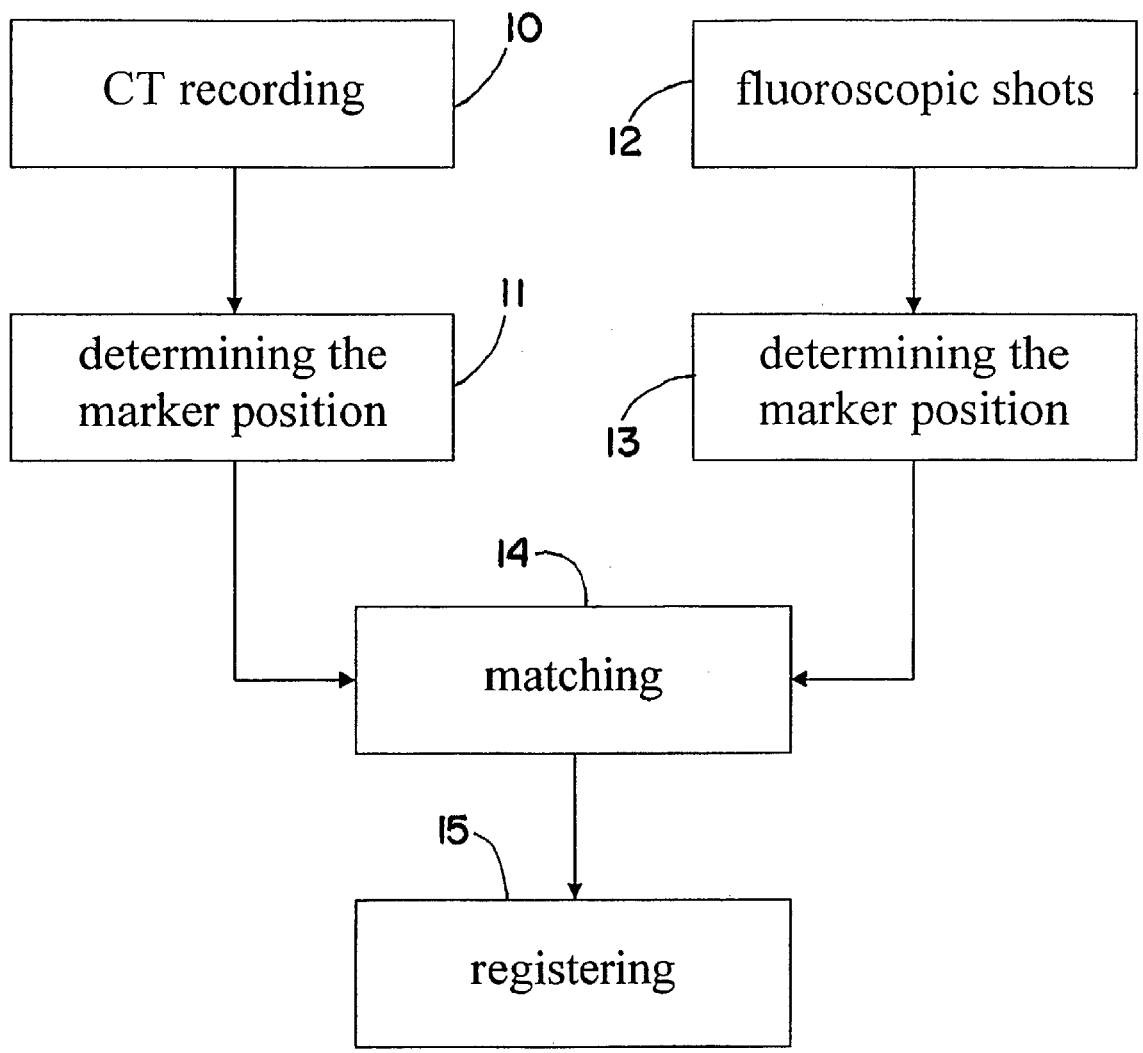
FIG. 5 is a flow diagram illustrating an exemplary method in accordance with the invention.

FIG. 5 shows a flow diagram of an exemplary method in accordance with the invention. A three-dimensional model of the structure, such as for example a hip, is generated by means of a CT recording at block 10, and the positions of the inserted markers are determined in the three-dimensional model at block 11. At block 12, calibrated fluoroscopic shots can be taken of the anatomical structure or pelvis from two different directions so as to obtain two two-dimensional x-ray recordings of the structure. The positions of the markers that are visible in the x-ray recordings are in turn ascertained at block 13. A known matching method then can be performed at block 14 in order to orientate the three-dimensional model ascertained from the CT recording in three-dimensional space or in the patient coordinate system. The matching method can use the locational information ascertained from the fluoroscopic shots, such that at block 15 the three-dimensional model of the structure matches the actual structure, thus registering the structure or pelvis.

Figure 6:
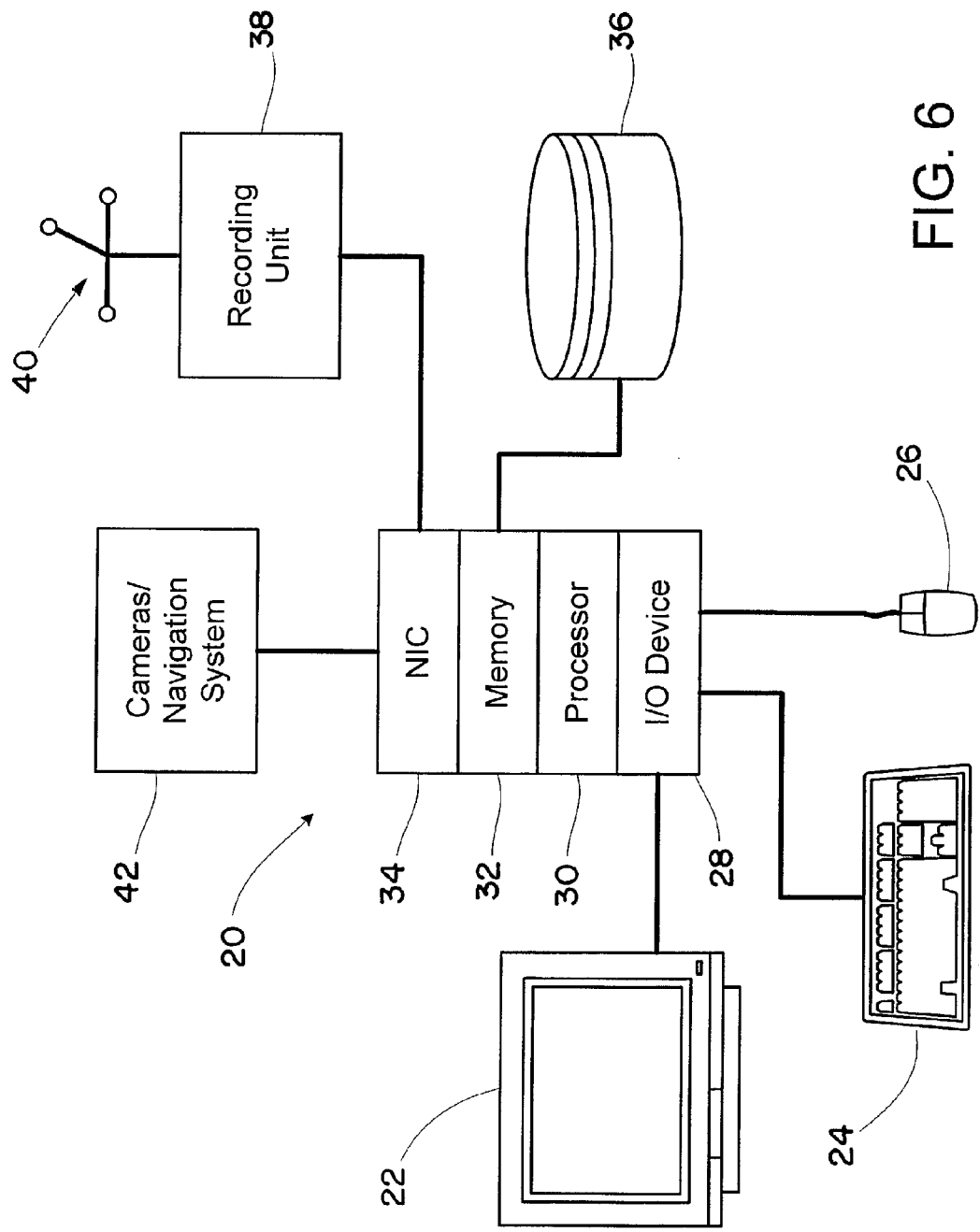
FIG. 6 is a block diagram of an exemplary computer system that can be used to implement the method described herein.

Moving now to FIG. 6 there is shown a block diagram of an exemplary computer 20 that may be used to implement the method described herein. The computer 20 may include a display 22 for viewing system information, and a keyboard 24 and pointing device 26 for data entry, screen navigation, etc. A computer mouse or other device that points to or otherwise identifies a location, action, etc., e.g., by a point and click method or some other method, are examples of a pointing device 26. Alternatively, a touch screen (not shown) may be used in place of the keyboard 24 and pointing device 26. The display 22, keyboard 24 and mouse 26 communicate with a processor via an input/output device 28, such as a video card and/or serial port (e.g., a USB port or the like).

A processor 30, such as an AMD Athlon 64® processor or an Intel Pentium IV® processor, combined with a memory 32 execute programs to perform various functions, such as data entry, numerical calculations, screen display, system setup, etc. The memory 32 may comprise several devices, including volatile and non-volatile memory components. Accordingly, the memory 32 may include, for example, random access memory (RAM), read-only memory (ROM), hard disks, floppy disks, optical disks (e.g., CDs and DVDs), tapes, flash devices and/or other memory components, plus associated drives, players and/or readers for the memory devices. The processor 30 and the memory 32 are coupled using a local interface (not shown). The local interface may be, for example, a data bus with accompanying control bus, a network, or other subsystem.

The memory may form part of a storage medium for storing information, such as application data, screen information, programs, etc., part of which may be in the form of a database 36. The database 36 may include data pertaining to a three-dimensional model of a structure to be registered. The storage medium may be a hard drive, for example, or any other storage means that can retain data, including other magnetic and/or optical storage devices. A network interface card (NIC) 34 allows the computer 20 to communicate with other devices.

Communicatively coupled to the computer 20 is a recording unit 38, such as a a calibrated x-ray source and a corresponding calibrated detector (e.g., a calibrated C-arm). The recording unit 38 also can include a reference array 40 or the like attached thereto. The reference array 40 enables a spatial location of the recording unit to be ascertain by a navigation system 42, for example.

A person having ordinary skill in the art of computer programming and applications of programming for computer systems would be able in view of the description provided herein to program a computer system 20 to operate and to carry out the functions described herein. Accordingly, details as to the specific programming code have been omitted for the sake of brevity. Also, while software in the memory 32 or in some other memory of the computer and/or server may be used to allow the system to carry out the functions and features described herein in accordance with the preferred embodiment of the invention, such functions and features also could be carried out via dedicated hardware, firmware, software, or combinations thereof, without departing from the scope of the invention.

Computer program elements of the invention may be embodied in hardware and/or in software (including firmware, resident software, micro-code, etc.). The invention may take the form of a computer program product, which can be embodied by a computer-usable or computer-readable storage medium having computer-usable or computer-readable program instructions, "code" or a "computer program" embodied in the medium for use by or in connection with the instruction execution system. In the context of this document, a computer-usable or computer-readable medium may be any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium such as the Internet. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner. The computer program product and any software and hardware described herein form the various means for carrying out the functions of the invention in the example embodiments.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for registering an anatomical structure using at least one marker attached to the anatomical structure, comprising:
    obtaining a three-dimensional model of the structure and the at least one marker via an imaging method, the at least one marker attached to the anatomical structure at least while the structure is imaged;
    obtaining at least two two-dimensional recordings of the structure and the at least one marker from different angles; and
    ascertaining a spatial position and location of the three-dimensional model or a position and location of the three-dimensional model in a patient coordinate system based on a matching method that matches the at least one marker in the three-dimensional model with an ascertained position of the at least one marker in the at least two two-dimensional mappings such that the three-dimensional model of the anatomical structure matches the anatomical structure.

2. The method according to claim 1, wherein the matching method ascertains the position of the at least one marker in each of the two-dimensional recordings of the structure, and
    wherein ascertaining the spatial position and location of the three-dimensional model or the position and location of the three-dimensional model in the patient coordinate system includes rear-projecting the marker positions ascertained in the two-dimensional recordings.

3. The method according to claim 1, wherein the matching method ascertains the position of the at least one marker in the three-dimensional recording, and the three-dimensional model of the structure is orientated such that the at least one marker of the three-dimensional model of the structure lies at each of the points ascertained by rear-projecting the positions of the at least one marker that is identifiable in the two-dimensional recordings.

4. The method according to claim 1, wherein obtaining at least two two-dimensional recordings includes calibrating the at least two two-dimensional recordings.

5. The method according to claim 1, wherein the three-dimensional recording of the structure is a computer tomography (CT) recording or nuclear spin resonance (MR) recording.

6. The method according to claim 1, wherein the at least one marker comprises a spherical object, a cuboid object or an edged object.

7. The method according to claim 1, wherein the at least one marker is formed from a radio-opaque material.

8. The method according to claim 1, wherein the at least one marker is formed from tantalum.

9. The method according to claim 1, further comprising embedding the at least one marker within the anatomical structure prior to obtaining the at least two two-dimensional recordings.

10. The method according to claim 9, wherein embedding includes injecting the marker into the anatomical structure.

11. A method for defining points, straight lines or planes in registered 2D images of an object, comprising calculating, on the basis of at least one marker inserted into the object at known locations relative to the object, characteristic points, straight lines or planes of the object.

12. A computer program embodied on a non-transitory computer readable medium for registering an anatomical structure using at least one marker attached to the anatomical structure, comprising:
  code that directs the acquisition of a three-dimensional model of the structure and the at least one marker via an imaging method, the at least one marker attached to the anatomical structure at least while the structure is imaged;
  code that directs the acquisition of at least two two-dimensional recordings of the structure and the at least one marker from different angles; and
  code that ascertains a spatial position and location of the three-dimensional model or a position and location of the three-dimensional model in a patient coordinate system based on a matching method that matches the at least one marker in the three-dimensional model with an ascertained position of the at least one marker in the at least two two-dimensional mappings such that the three-dimensional model of the anatomical structure matches the anatomical structure.

13. A device for registering a structure having at least one marker attached thereto, comprising:
  a recording unit for generating two-dimensional mappings; and
  a computational unit operatively coupled to the recording unit, said computational unit including
  a processor and memory,
  a three-dimensional model of the structure stored in memory,
  logic stored in memory and executable by the processor, said logic including
  logic that directs the recording unit to acquire at least two two-dimensional recordings of the structure and the at least one marker from different angles, the at least one marker attached to the anatomical structure at least while the structure is imaged;
  logic that ascertains a spatial position and location of the three-dimensional model or a position and location of the three-dimensional model in a patient coordinate system based on a matching method that matches the at least one marker in the three-dimensional model with an ascertained position of the at least one marker in the at least two two-dimensional mappings such that the three-dimensional model of the anatomical structure matches the anatomical structure.

14. The device according to claim 13, wherein one or more markers are attached to the recording unit to enable generation of calibrated recordings.

15. The device according to claim 13, comprising a navigation system operative to track a position of the one or more markers.

16. The method according to claim 1, wherein the at least one marker comprises a plurality of markers.

* * * * *